United States Patent [19]
Roe et al.

[11] Patent Number: 5,653,703
[45] Date of Patent: Aug. 5, 1997

[54] ABSORBENT ARTICLE HAVING ANGULAR UPSTANDING TRANSVERSE PARTITION

[75] Inventors: Donald Carroll Roe, West Chester; Michael Payne, Cincinnati; John Joseph Litchholt, Harrison, all of Ohio

[73] Assignee: The Procter & Gamble Company, Cincinnati, Ohio

[21] Appl. No.: 664,603

[22] Filed: Jun. 18, 1996

Related U.S. Application Data

[63] Continuation-in-part of Ser. No. 347,026, Nov. 30, 1994, Pat. No. 5,554,142.

[51] Int. Cl.⁶ .............................. A61F 13/15; A61F 13/20
[52] U.S. Cl. ........................ 604/385.1; 604/385.2
[58] Field of Search ..................... 604/385.1, 385.2, 604/358, 378

[56] References Cited

U.S. PATENT DOCUMENTS

| | | | |
|---|---|---|---|
| 4,895,568 | 1/1990 | Enloe | 604/385.1 |
| 4,925,453 | 5/1990 | Kannankeril | 604/385.1 |
| 4,950,263 | 8/1990 | Lewis | 604/385.1 |
| 5,389,095 | 2/1995 | Suzuki et al. | 604/385.2 |

FOREIGN PATENT DOCUMENTS

| | | |
|---|---|---|
| 0 585 904 A2 | 3/1994 | European Pat. Off. . |
| 2 287 393 | 9/1995 | United Kingdom . |
| 2 287 888 | 10/1995 | United Kingdom . |

*Primary Examiner*—David H. Willse
*Assistant Examiner*—Ki Yong O
*Attorney, Agent, or Firm*—Larry L. Huston; E. Kelly Linman; Jacobus C. Rasser

[57] ABSTRACT

A disposable absorbent article having a transverse partition. The transverse partition is upstanding from the topsheet and presents an abrupt discontinuity out of the plane of the disposable absorbent article and obstructs fecal material deposited in the rear portion of the disposable absorbent article from migrating to the from portion of the disposable absorbent article. This obstruction minimizes soiling of the genitalia of the wearer. The disposable absorbent article may have upstanding barrier leg cuffs. The transverse partition may connect the barrier leg cuffs to form an H-shape. The transverse partition forms an acute angle with the rear portion of the disposable absorbent article.

13 Claims, 2 Drawing Sheets

ABSORBENT ARTICLE HAVING ANGULAR UPSTANDING TRANSVERSE PARTITION

This application is a CIP which claims the benefit of U.S. patent application Ser. No. 347,026 filed Nov. 30, 1994, now U.S. Pat. No. 5,554,142, issued Sep. 10, 1996.

FIELD OF THE INVENTION

The present invention relates to disposable absorbent articles, and more particularly to disposable absorbent articles which minimize the migration of fecal material deposited thereon.

BACKGROUND OF THE INVENTION

Disposable absorbent articles, such as diapers, are well known in the art. Disposable absorbent articles retain and absorb body exudates, such as urine and fecal material deposited thereon.

Significant advances have been made in the art relative to absorbing and retaining urine deposits. For example, disposable absorbent articles seldom leak and may be relatively thin due to the incorporation of absorbent gelling materials.

However, fewer attempts have been made in the art to handle deposits of fecal material in disposable absorbent articles. Fecal material has the undesirable proclivities of smearing onto the wearer's skin, causing epidermal irritation and complicating the task of cleaning the wearer when the soiled diaper or other disposable absorbent article is removed.

To overcome these proclivities, certain attempts have been made in the art to isolate the fecal material from the skin of the wearer. Such attempts generally provide a void or hole into which the fecal material is deposited and retained (hopefully), so that the location of the fecal material is limited to the position of the void or hole. Examples of such attempts are found in U.S. Pat. 4,662,877 issued May 5, 1987, to Williams; U.S. Pat. No. 4,892,536 issued Jan. 9, 1990, to DesMarais et al.; U.S. Pat. No. 4,968,312 issued Nov. 6, 1990, to Khan; U.S. Pat. No. 4,990,147 issued Feb. 5, 1991, to Freeland; U.S. Pat. No. 5,062,840 issued Nov. 5, 1991, to Holt et at.

Other attempts have been made in the art to provide cups which attempt to circumscribe the anal opening, the genitalia, or both in an attempt to isolate these regions of the wearer's body. These attempts can be uncomfortable for the wearer and require precise positioning of the cup.

In still another attempt, resilient barriers extending transversely or longitudinally have been placed below the topsheet of the diaper. But this arrangement suffers from the drawback that fetal material deposited on the topsheet is above the barrier, can still migrate and still cause the aforementioned problems. This arrangement simply does not provide the abrupt discontinuity necessary to obstruct migration of fecal material deposited on the topsheet of the diaper.

Furthermore, such an arrangement may even be ineffective in preventing excessive transverse migration of the fecal material. A barrier disposed below the topsheet cannot be easily joined to longitudinally extending barrier leg cuffs, which, as are well known in the art, minimize leakage from the diaper. Thus, fecal material which is channeled towards transverse migration by the barrier may be transported to the perimeter of the diaper and breach the perimeter, causing leakage.

Furthermore, it has been found that not only must the transverse partition be disposed above the topsheet, if the transverse partition extends from the topsheet at a substantially 90 degree angle, it will be ineffective in preventing the migration of fetal material from the rear portion of the disposable absorbent article to the front portion of the disposable absorbent article. Thus, the transverse partition must be predisposed to form a pocket to capture and isolate fecal material in the rear portion of the disposable absorbent article.

Accordingly, it is an object of this invention to provide a disposable absorbent article having a transverse partition which may be used in conjunction with other components of the disposable absorbent article, such as barrier leg cuffs, to minimize leakage. It is further an object of this invention to provide a disposable absorbent article which limits the migration of fecal material, thereby reducing epidermal contact with the fecal material and minimizing cleaning by the caretaker. Finally, it is an object of this invention to provide an abrupt surface discontinuity in a disposable absorbent article to obstruct the flow of fecal material in the longitudinal direction.

BRIEF SUMMARY OF THE INVENTION

The present invention comprises a disposable absorbent article, such as a diaper. The disposable absorbent article has a liquid previous topsheet with an outwardly oriented body facing surface which is oriented towards the wearer while in use and a core facing surface opposed to the body facing surface. The disposable absorbent article further comprises a liquid impervious backsheet at least partially peripherally joined to the topsheet and an absorbent core intermediate the topsheet and the backsheet.

The disposable absorbent article further comprises a transverse partition disposed on the body facing surface of the topsheet and extending outwardly therefrom, to be upstanding and extend away from the plane of the disposable absorbent article. The transverse partition divides the disposable absorbent article into a front portion and a rear portion, and presents an abrupt discontinuity between the front portion and the rear portion. The transverse partition is angled towards the rear portion of the disposable absorbent article at an acute angle. The acute angle is from 45 to 85 degrees with respect to the body facing surface of the topsheet, and preferably from 55 to 80 degrees with respect to the body facing surface of the topsheet. Fecal material deposited in the rear portion of the disposable absorbent article is obstructed from longitudinally migrating to the front portion of the disposable absorbent article by the transverse partition.

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and liner. A preferred embodiment of an absorbent article of the present invention is the unitary disposable absorbent article, diaper 20, shown in FIG. 1. As used herein, the term "diaper" refers to an absorbent article generally worn by infants or incontinent persons about the lower torso of the wearer. It should be understood, however, that the present invention is also applicable to other absorbent articles such as incontinent briefs, incontinent undergarments, diaper holders and liners, certain feminine hygiene garments, and the like.

Figure 1:
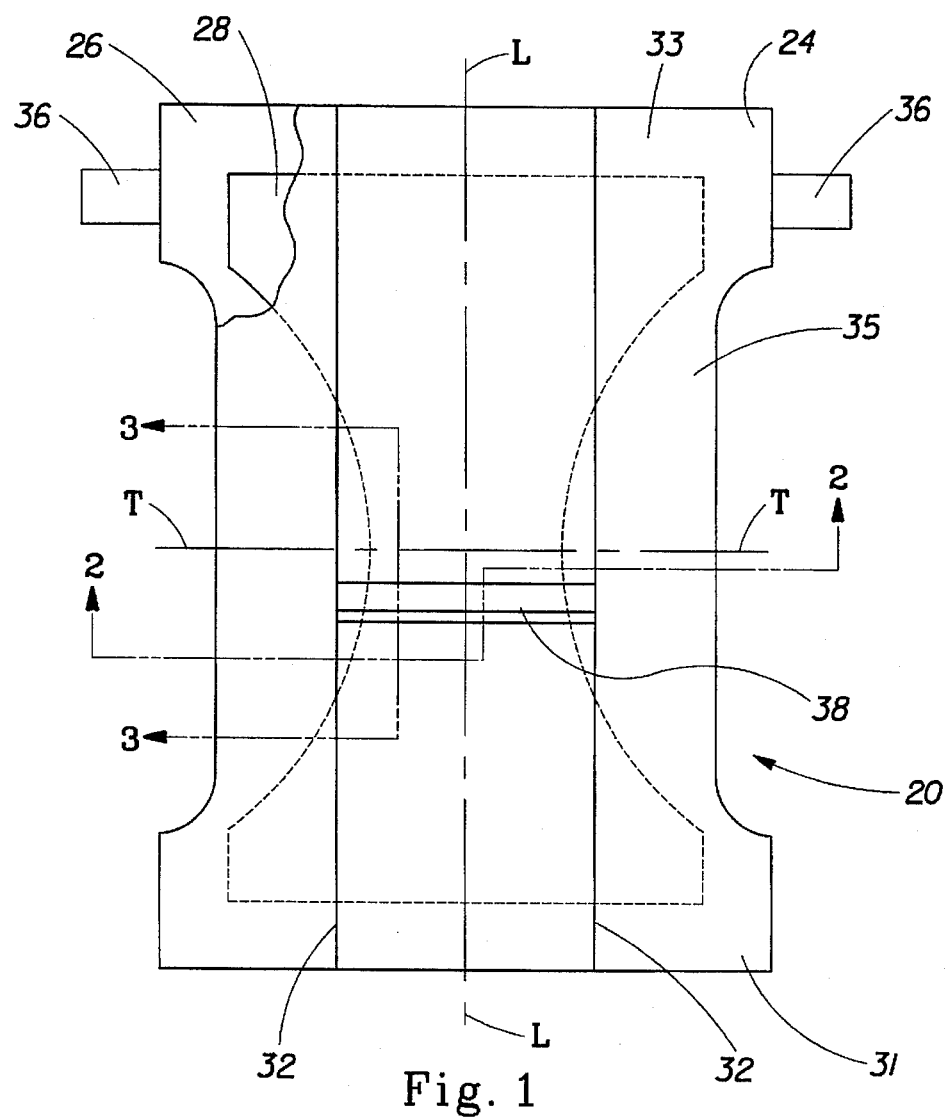
FIG. 1 is top plan view of a disposable absorbent article according to the present invention shown partially in cut-away and having no elastic induced contraction.

FIG. 1 is a plan view of the diaper 20 of the present invention in its flat-out, uncontracted state (i.e., with elastic induced contraction pulled out) with portions of the structure being cut-away to more clearly show the construction of the diaper 20 and with the portion of the diaper 20 which faces or contacts the wearer, the inner surface, oriented towards the viewer. As shown in FIG. 1, the diaper 20 preferably comprises a liquid previous topsheet 24; a liquid impervious backsheet 26 joined with the topsheet 24; an absorbent core 28 positioned between the topsheet 24 and the backsheet 26; elasticized barrier leg cuffs 32; a fastening system generally multiply designated as 36; and an upstanding transverse partition 38.

The topsheet 24 of the diaper 20 has an outwardly oriented body facing surface which faces (and usually contacts) the wearer while the diaper 20 is in use and a core facing surface opposed to the body facing surface. The body facing surface of the topsheet 24 of the diaper 20 comprises that portion of the diaper 20 which is positioned adjacent the wearer's body during use (i.e., the inner surface generally is formed by both at least a portion of the topsheet 24 and other components joined to the topsheet 24). The diaper 20 further has a first waist region 31 oriented towards the front of the wearer while the diaper is in use, a second waist region 33 longitudinally opposite the first waist region 31, a crotch region 35 positioned between the first waist region 31 and the second waist region 33, and a periphery which is defined by the outer edges of the diaper 20.

The diaper 20 has a longitudinal centerline L—L which divides the diaper 20 into left and right halves, and which divides the standing wearer into left and right body halves. The diaper 20 further comprises a transverse centerline T—T orthogonal to the longitudinal centerline L—L which divides the diaper 20 into a from portion and a rear portion. The transverse centerline T—T is midway between the front and rear longitudinal extremities of the diaper chassis. Orthogonal to the mutually perpendicular longitudinal centerline L—L and transverse centerline T—T, is a Z-direction axis, which extends outwardly from the plane of the diaper 20.

A component of the diaper 20 is considered to be transversely oriented, and hence "transverse" if such component forms an angle of ±45 degrees or less with the transverse centerline T—T. Similarly, a component is considered to be longitudinally oriented, and hence "longitudinal" if such component forms an angle of ±45 degrees or less with the longitudinal centerline L—L.

FIG. 1 shows a preferred embodiment of the diaper 20 in which the topsheet 24 and the backsheet 26 have length and width dimensions generally larger than those of the absorbent core 28. The topsheet 24 and the backsheet 26 extend beyond the edges of the absorbent core 28 to thereby form the periphery of the diaper 20. While the topsheet 24, the backsheet 26, and the absorbent core 28 may be assembled in a variety of well known configurations, preferred diaper configurations are described generally in U.S. Pat. No. 3,860,003 entitled "Contractable Side Portions for Disposable Diaper" which issued to Kenneth B. on Jan. 14, 1975, which is incorporated herein by reference.

The absorbent core 28 may be any absorbent means which is generally compressible, conformable, non-irritating to the wearer's skin, and capable of absorbing and retaining liquids such as urine and other certain body exudates. As shown in FIG. 1, the absorbent core 28 has a garment surface, a body surface, side edges, and waist edges. The absorbent core 28 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials. The configuration and construction of the absorbent core may also be varied (e.g., the absorbent core may have varying caliper zones, a hydrophilic gradient, a superabsorbent gradient, or lower average density and lower average basis weight acquisition zones; or may comprise one or more layers or structures). The total absorbent capacity of the absorbent core 28 should, however, be compatible with the design loading and the intended use of the diaper 20. Further, the size and absorbent capacity of the absorbent core 28 may be varied to accommodate wearers ranging from infants through adults. Exemplary absorbent structures for use as the absorbent core 28 are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual Layered Cores" issued to Weisman et at. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et at. on May 30, 1989. Each of these patents are incorporated herein by reference.

The backsheet 26 is positioned adjacent the garment surface of the absorbent core 28 and is preferably joined thereto by attachment means (not shown) such as those well known in the art. For example, the backsheet 26 may be secured to the absorbent core 28 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and are marketed as HL-1258. The attachment means will preferably comprise an open pattern network of filaments of adhesive as is disclosed in U.S. Pat. No. 4,573,986 entitled "Disposable Waste-Containment Garment", which issued to Minetola et at. on Mar. 4, 1986, more preferably several lines of adhesive filaments swirled into a spiral pattern such as is illustrated by the apparatus and methods shown in U.S. Pat. No. 3,911,173 issued to Sprague, Jr. on Oct. 7, 1975; U.S. Pat. No. 4,785,996 issued to Ziecker, et at. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 26 is impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body. The backsheet 26 prevents the exudates absorbed and contained in the absorbent core 28 from wetting articles which contact the diaper 20 such as bed-sheets and undergarments. The backsheet 26 may thus comprise a woven or nonwoven material, polymeric films such as thermoplastic films of polyethylene or polypropylene, or composite materials such as a film-coated nonwoven material. Preferably, the backsheet is a thermoplastic film having a thickness of from about 0.012 mm (0.5 mil) to about 0.051 mm (2.0 mils). Particularly preferred materials for the backsheet include RR8220 blown films and RR5475 cast films as manufactured by Tredegar Industries, Inc. of Terre Haute, IN. The backsheet 26 is preferably embossed and/or matte finished to provide a more clothlike appearance. Further, the backsheet 26 may permit vapors to escape from the absorbent core 28 (i.e., breathable) while still preventing exudates from passing through the backsheet 26. The topsheet 24 is positioned adjacent the body surface of the absorbent core 28 and is preferably at least partially peripherally joined thereto and to the backsheet 26 by attachment means (not shown) such as those well known in the art. Suitable attachment means are described with respect to joining the backsheet 26 to the absorbent core 28. As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. In a preferred embodiment of the present invention, the topsheet 24 and the backsheet 26 are joined directly to each other in the diaper periphery and are indirectly joined together as a result of their joinder to the absorbent core 28 by suitable attachment means (not shown).

The topsheet 24 is compliant, soft feeling, and non-irritating to the wearer's skin. Further, the topsheet 24 is liquid previous permitting liquids (e.g., urine) to readily penetrate through its thickness. A suitable topsheet may be manufactured from a wide range of materials, such as porous foams; reticulated foams; apertured plastic films; or woven or nonwoven webs of natural fibers (e.g., wood or cotton fibers), synthetic fibers (e.g., polyester, polyethylene, or polypropylene fibers), or a combination of natural and synthetic fibers. Preferably, the topsheet 24 is made of a hydrophobic material to isolate the wearer's skin from liquids contained in the absorbent core 28. There are a number of manufacturing techniques which may be used to manufacture the topsheet 24. For example, the topsheet 24 may be a nonwoven web of fibers spunbonded, carded, wet-laid, meltblown, hydroentangled, combinations of the above, or the like. A preferred topsheet is carded and thermally bonded by means well known to those skilled in the fabrics art. A preferred topsheet comprises a web of staple length polypropylene fibers such as is manufactured by Veratec, Inc., a Division of International Paper Company, of Walpole, Mass. under the designation P-8.

The diaper 20 preferably further comprises elasticized barrier leg cuffs 32 for providing improved containment of liquids and other body exudates. Each elasticized barrier leg cuff 32 may comprise several different embodiments for reducing the leakage of body exudates from the leg regions of the diaper 20. U.S. Pat. No. 4,909,803 entitled "Disposable Absorbent Article Having Elasticized Flaps" issued to Aziz et al. on Mar. 20, 1990, describes a disposable diaper 20 having "stand-up" elasticized flaps (barrier leg cuffs 32) to improve the containment of the leg regions of the diaper 20. U.S. Pat. No. 4,695,278 entitled "Absorbent Article Having Dual Cuffs" issued to Lawson on Sep. 22, 1987, describes a disposable diaper 20 having dual cuffs including both a gasketing cuff and a barrier cuff 32. Both of these patents are incorporated herein by reference for the purpose of showing suitable exemplary constructions for the barrier leg cuffs 32.

Spanning the transverse distance between the barrier leg cuffs 32 is an upstanding transverse partition 38. The transverse partition 38 is disposed on the body facing surface of the topsheet 24 and extending outwardly therefrom to present an abrupt discontinuity in the body facing surface of the topsheet 24. As illustrated, preferably the transverse partition 38 is generally straight, rectilinear, transverse and preferably parallel to the transverse centerline T—T of the diaper 20. If desired, the transverse pattern 38 may even be coincident with the transverse centerline T—T of the diaper 20.

The transverse partition 38 obstructs the longitudinal migration of fecal material deposited in the rear portion of the diaper 20 towards the front portion of the diaper 20. Preferably the upstanding partition 38 connects the barrier leg cuffs 32, forming an H-shape. This arrangement is highly preferred because it prevents seepage of fecal material around the edges of the transverse partition and contains the fecal material in the rear portion of the diaper 20.

Figure 2:
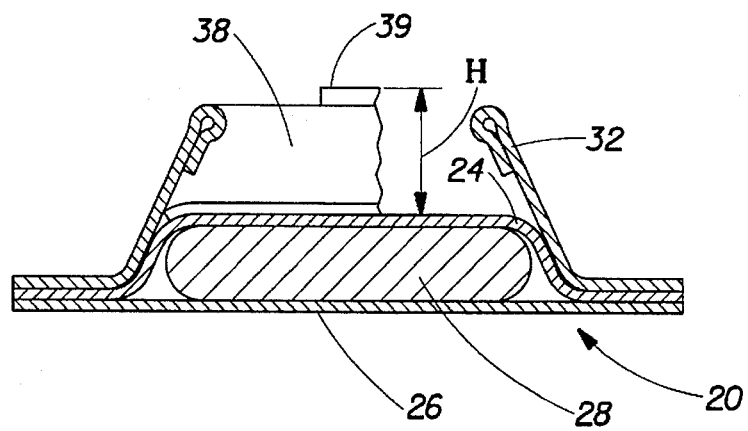
FIG. 2 is an offset vertical sectional view taken along line 2—2 of FIG. 1, and showing the addition of a spacer to the transverse partition.

Referring to FIG. 2, the transverse partition 38 has a proximal edge which is preferably joined to the topsheet 24, and particularly the body facing surface thereof, by adhesive, by autogeneous bonding, such as is disclosed in commonly assigned U.S. Pat. No. 4,854,984 issued to Ball et al, which patent is incorporated herein by reference, or by other joining means, as are well known in the art. The transverse partition 38 extends outwardly from the plane of the topsheet 24 with a vector component in the Z-direction to a distal edge.

It is important the transverse partition 38 be upstanding and rise above the plane of the topsheet 24 to an effective height H sufficient to present an abrupt discontinuity to obstruct the longitudinal movement of fecal material while the diaper 20 is worn. It is to be recognized that if the topsheet 24 has wrinkles, rugosities, undulations, or other deviations from planarity, these should be taken into account at the position of the transverse partition 38 when determining its effective height H. Otherwise such deviations from planarity in the topsheet 24 may diminish the effective height H of the distal edge of the partition 38 above the topsheet 24, and not sufficiently obstruct the flow of fecal material.

As used herein, the "effective height" is the Z-direction distance from the proximal edge of the transverse partition 38 to the distal edge of the transverse partition 38. The transverse partition 38 preferably has an effective height H above to the body facing surface of the topsheet 24 of at least 1 inch, more preferably 1.2 to 2.0 inches, and most preferably 1.6 to 1.8 inches. It is important the effective height H of the transverse partition 38 be within the aforementioned range. If the effective height H of the transverse partition 38 is too small, fecal material will move over the top of the transverse partition 38, and smear onto the genitalia of the wearer. Conversely, if the effective height H of the transverse partition 38 is too great, the transverse partition 38 will be bulky and uncomfortable to the wearer. In use, the distal edge of the transverse partition 38 is preferably placed between the anal opening and genitalia of the wearer. Therefore, the partition should be disposed on the topsheet 24 to accommodate this position during wear.

Figure 3:
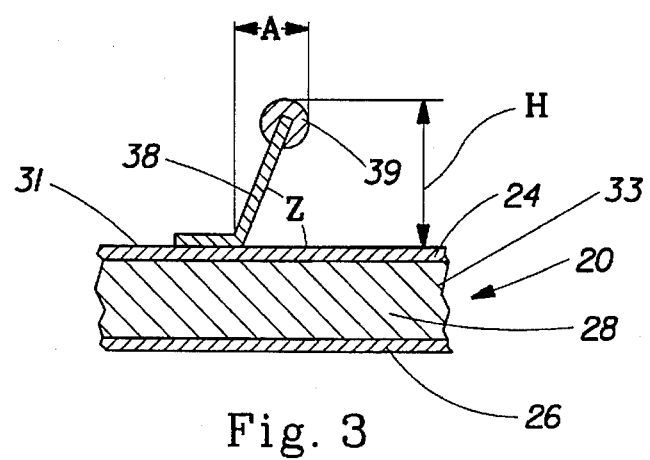
FIG. 3 is a fragmentary instant vertical sectional view taken along line 3—3 of FIG. 1, also showing the addition of a spacer to the transverse partition.

As illustrated in FIG. 3, the transverse partition 38 is preferably not orthogonal to the plane of the topsheet 24, but instead is disposed in angular relationship therewith so that the distal edge of the upstanding transverse partition 38 is oriented towards the rear portion and the rear waist margin 33 of the diaper 20. This arrangement provides the advantage that the pressure of the fetal material helps seal the transverse partition 38 against the wearer's body, minimizing the leakage of fecal material across the transverse partition 38. This arrangement further minimizes the vertical forces necessary to maintain the transverse partition 38 in contact with the body of the wearer.

The transverse partition 38 has two opposed faces, a front facing surface and a rearward facing surface. The rearward facing surface forms an acute angle Z with the body facing surface of the topsheet. The acute angle Z is preferably from 45 to 85 degrees, and more preferably from 55 to 80 degrees, and most preferably from 65 to 75 degrees.

It is important the acute angle Z be within the aforementioned range. If the acute angle Z is too small, the transverse partition 38 will not present an effective barrier to fetal material. Additionally, the fecal material may be deposited on the front facing surface of the transverse partition 38, and further smear onto the genitals of the wearer. Alternatively, if the angle of the transverse partition 38 is too great, no pocket will be formed, particularly when the wearer sits on the diaper 20. Therefore, the acute angle Z must be within the aforementioned range, to collapse backwards and thereby contain the fetal material in the rear portion of the diaper 20.

Figure 4:
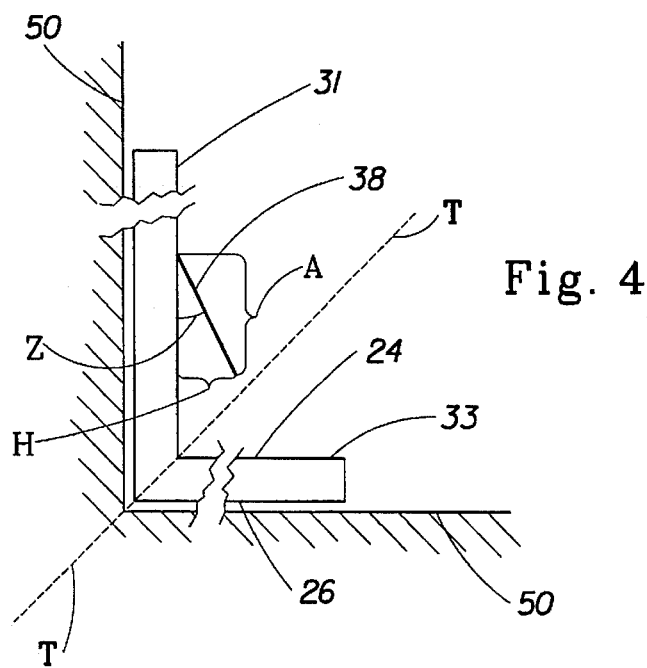
FIG. 4 is a schematic side view of a diaper being tested to determine the acute angle of the transverse partition.
Figures 5A, 5B, 5C, 5D:
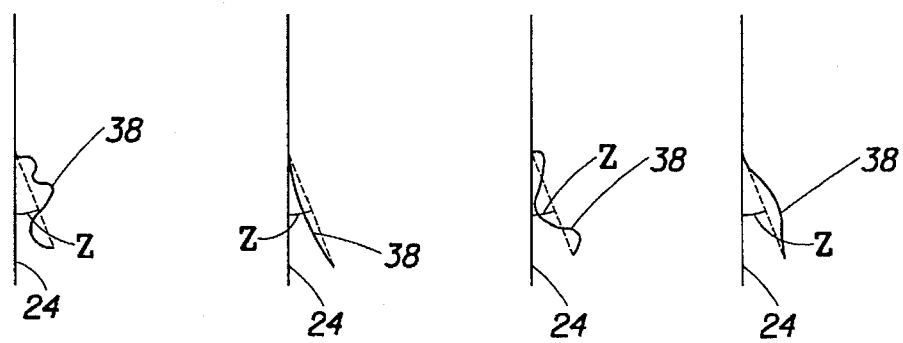
FIGS. 5A, 5B, 5C, and 5D are schematic side views of three transverse partitions having identical included angles.

Referring to FIG. 4, the acute angle Z of the transverse partition 38 is determined as follows. The disposable absorbent article is attached to a 90 degree frame 50 using ordinary tape. The front portion, i.e., the first waist region 31, of the diaper 20 is vertically oriented on the frame, while the rear portion, i.e., the second waist region 33, is maintained horizontal. The transverse centerline T—T of the diaper 20 is disposed at the vertex of the frame 50.

The projected distance A, taken parallel to the plane of the topsheet 24, from the proximal edge to the distal edge of the transverse partition 38 is measured, using a laboratory ruler. Likewise, the effective height H of the transverse partition 38 is measured. The effective height H and the projected distance A are measured parallel to the vertical and horizontal walls of the frame 50, respectively. The acute angle Z of the transverse partition 38 is found by the arctan (H/A). All measurements are taken coincident the longitudinal centerline L—L of the transverse partition 38. In making the measurement, the transverse partition 38 is allowed to form its natural shape, particularly as may be dictated by the barrier leg cuffs 32.

Referring to FIGS. 5A, 5B, 5C, and 5D, if the transverse partition 38 is not straight, but rather, has rugosities or irregularities, these are not considered in measuring the projected distance A and the effective height H. Only the projected triangulated distances between the proximal and distal edges of the transverse partition 38 are considered. If the projected distance A of the transverse partition 38 is great enough that the distal edge of the transverse partition 38 contacts the horizontal portion of the frame 50, the transverse partition 38 is moved upwards on the vertical wall of the frame 50, until the transverse partition 38 clears the horizontal wall of the frame 50. However, it is to be recognized this is an unusual circumstance, and the measurement is ordinarily taken with the transverse centerline T—T disposed at the vertex of the frame 50.

The transverse partition 38 may be made of a water previous material, but is preferably made of a liquid impermeable material. The liquid impermeable material prevents (or minimizes the amount of) runny fecal material reaching the genitalia of the wearer. Nonwoven materials, such as those commonly used to form the barrier leg cuffs 32, have been found to be particularly suitable in the transverse partition 38. Other suitable materials for the transverse partition 38 include foams, formed films, etc. A suitable liquid impermeable material, particularly a liquid impermeable nonwoven material for the transverse partition 38 may be obtained from the Veratec Corporation of Walpole, Mass. as a hydrophobic P-8 material having a basis weight of at least 20 grams per square meter. If desired, a high basis weight spun/meltblown/spun layered web made of polypropylene or polyethylene as is available from Fiberweb Corporation under the name Eclipse could be used. Alternatively, Veratec Everspun nonwoven material may be used.

If desired, small discrete styrofoam beads may be placed in a water impervious casing to form the transverse partition 38. This arrangement provides a partition which conforms to the groove between the legs of the wearer, particularly the female wearer, and allows the transverse partition to fit into such groove. Such fitting of the transverse partition 38 to the grooves of the wearer's body (which is typically a continuation of the gluteal groove) minimizes the flow channel beyond the transverse partition 38 through which fecal material may be transported to the front portion of the diaper 20. A transverse partition 38 having discrete styrofoam beads may be made in accordance with the teachings of commonly assigned U.S. Pat. No. 5,306,266 issued Apr. 26, 1994 to Freeland, the disclosure of which is incorporated herein by reference.

If desired, a transverse linear elastic strand may be applied to the distal edge of the transverse partition 38 to provide transverse contraction. Optionally, a foam cap (not shown) may be applied to the distal edge of the transverse partition 38 to increase wearer comfort. The foam cap may be elastically extensible in the transverse direction, as illustrated.

If desired, spacers 39 may be added to the distal edge of the transverse partition 38 to locally increase its effective height H. The spacers 39 may be made and disposed on the transverse partition 38 according to commonly assigned U.S. application Ser. No. 08/347,026, Issue Batch. No. V31, filed Nov. 30, 1994 in the names of Dreier et al., now U.S. Pat. No. 5,554,142, issued Sep. 10, 1996 the disclosure of which is incorporated herein by reference.

It will be obvious to one skilled in the art that other variations and arrangements are feasible and within the scope of the claimed invention. For example, the transverse partition 38 need not necessarily be rectilinear, but may be curvilinear. Generally if a curvilinear transverse partition 38 is selected, it should be concave towards the rear portion 33 of the diaper 20. Elastic strands may be applied to the transverse partition 38 in the vertical direction or in a fan-shaped arrangement radiating outwardly from the center of the proximal edge of the transverse partition 38. The transverse partition 38 may have small gaps juxtaposed with the barrier leg cuffs 32, to allow flow of fecal material from the rear portion of the diaper 20 to the front portion of the diaper 20 in the event of heavy loading between diaper 20 changes. Such gaps provide a safety valve to prevent the fecal material from breaching the perimeter of the diaper 20. All such variations are within the scope of the appended claims.

The diaper 20 is preferably applied to a wearer by positioning one of the waist regions 31 or 33, preferably the second waist region 33 (which typically has the fastening system 36), under the wearer's back and drawing the remainder of the diaper 20 between the wearer's legs so that the other waist region 31, preferably the first waist region 31, is positioned across the from of the wearer. The tape tabs of the fastening system are then released from the release portion. The diaperer then wraps the elasticized side panel around the wearer, while still grasping the tab portion. The elasticized side panels will typically be extended and tensioned during this operation so as to conform to the size and shape of the wearer. The fastening system 36 is secured to the outer surface of the diaper 20 to effect a side closure.

What is claimed is:

1. A disposable absorbent article having a longitudinal centerline and a transverse centerline orthogonal thereto, said disposable absorbent article comprising:

a liquid previous topsheet having an outwardly oriented body facing surface and a core facing surface opposed thereto;

a liquid impervious backsheet at least partially peripherally joined to said topsheet;

an absorbent core intermediate said topsheet and said backsheet; and a transverse partition disposed on said body facing surface of said topsheet and extending outwardly therefrom, said transverse partition dividing said disposable absorbent article into a front portion and a rear portion, said front region having a front waist portion and said rear region having a rear waist portion whereby fecal material deposited in said rear portion of said disposable absorbent article is obstructed from migrating to said front portion of said disposable absorbent article, said transverse partition having a front facing surface and a rearward facing surface, whereby when said disposable absorbent article is attached to a 90 degree frame having a vertical leg, a horizontal leg and a vertex such that said front waist region and transverse partition are vertically oriented on said vertical leg of said frame and said rear waist region is horizontally oriented on said horizontal leg of said frame and said transverse centerline of said diaper is disposed at said vertex of said frame, said rearward facing surface of said transverse partition maintains an acute angle with said body facing surface of said topsheet, said acute angle being from 45 degrees to 85 degrees.

2. A disposable absorbent article having a longitudinal centerline and a transverse centerline orthogonal thereto, said disposable absorbent article comprising:

a liquid previous topsheet having an outwardly oriented body facing surface and a core facing surface opposed thereto;

a liquid impervious backsheet at least partially peripherally joined to said topsheet; an absorbent core intermediate said topsheet and said backsheet;

two longitudinally oriented barrier leg cuffs upstanding from the plane of said topsheet and being spaced apart in the transverse direction; and a transverse partition disposed on said body facing surface of said topsheet and connecting said two longitudinally oriented barrier leg cuffs extending outwardly therefrom, said transverse partition dividing said disposable absorbent article into a front portion and a rear portion, said front region having a front waist portion and said rear portion having a rear waist region whereby fecal material deposited in said rear portion of said disposable absorbent article is obstructed from migrating to said front portion of said disposable absorbent article, said transverse partition having a front facing surface and a rearward facing surface, whereby when said disposable absorbent article is attached to a 90 degree frame having a vertical leg, a horizontal leg and a vertex such that said front waist region and transverse partition are vertically oriented on said vertical leg of said frame and said rear waist region is horizontally oriented on said horizontal leg of said frame and said transverse centerline of said diaper is disposed at said vertex of said frame, said rearward facing surface of said transverse partition maintains an acute angle with said body facing surface of said topsheet, said acute angle being from 45 degrees to 85 degrees.

3. A disposable absorbent article according to claims 1 or 2 wherein said acute angle is from 55 degrees to 80 degrees.

4. A disposable absorbent article according to claim 3 wherein said acute angle is from 65 degrees to 75 degrees.

5. A disposable absorbent article according to claims 1 or 2 wherein said transverse partition has an effective height of at least one inch.

6. A disposable absorbent article according to claim 5 wherein said transverse partition has an effective height of 1.2 to 2.0 inches.

7. A disposable absorbent article according to claim 6 wherein said transverse partition has an effective height of 1.6 to 1.8 inches.

8. A disposable absorbent article according to claims 1 or 2 wherein said transverse partition is joined to said body facing surface of said topsheet and extends outwardly therefrom to a distal edge disposed at an effective height above said topsheet, said transverse partition further comprising at least one spacer on said distal edge of said transverse partition, whereby said spacers increase the effective height of said transverse partition at the position of said spacer.

9. A disposable absorbent article according to claim 8 wherein said transverse partition is elastically extensible in said transverse direction.

10. A disposable absorbent article according to claims 1 or 2 wherein said transverse partition is liquid impermeable.

11. A disposable absorbent article having a longitudinal centerline and a transverse centerline orthogonal thereto, said disposable absorbent article comprising:

a liquid previous topsheet having an outwardly oriented body facing surface and a core facing surface opposed thereto;

a liquid impervious backsheet at least partially peripherally joined to said topsheet;

an absorbent core intermediate said topsheet and said backsheet;

two longitudinally oriented barrier leg cuffs upstanding from the plane of said topsheet and being spaced apart in the transverse direction; and a liquid impermeable transverse partition disposed on said body facing surface of said topsheet and connecting said two longitudinally oriented barrier leg cuffs extending outwardly therefrom, said transverse partition dividing said disposable absorbent article into a front portion and a rear portion, said front portion having a front waist portion and said rear region having a rear waist region whereby fecal material deposited in said rear portion of said disposable absorbent article is obstructed from migrating to said front portion of said disposable absorbent article, said transverse partition having a front facing surface and a rearward facing surface, whereby when said disposable absorbent article is attached to a 90 degree frame having a vertical leg, a horizontal leg and a vertex such that said front waist region and transverse partition are vertically oriented on said vertical leg of said frame and said rear waist region is horizontally oriented on said horizontal leg of said frame and said transverse centerline of said diaper is disposed at said vertex of said frame, said rearward facing surface of said transverse partition maintains an acute angle with said body facing surface of said topsheet, said acute angle being from 45 degrees to 85 degrees.

12. A disposable absorbent article according to claim 11 wherein said transverse partition has an effective height of 1.2 to 2 inches.

13. A disposable absorbent article according to claim 11 wherein said acute angle is from 65 to 75 degrees.

* * * * *

UNITED STATES PATENT AND TRADEMARK OFFICE
CERTIFICATE OF CORRECTION

PATENT NO. : 5,653,703
DATED : August 5, 1997
INVENTOR(S) : DONALD CARROLL ROE ET AL.

It is certified that error appears in the above-identified patent and that said Letters Patent is hereby corrected as shown below:

Cover page of patent, under References Cited, U.S. PATENT DOCUMENTS, add the following: --

4,662,877    5/87    Williams............604/385

4,892,536    1/90    Desmarais et al......604/385.2

4,968,312    11/90    Kahn................604.388.1

4,990,147    2/91    Freeland............604/385.2

5,062,840    11/91    Holt et al............604/385.1 --.

Cover page of patent, under References Cited, FOREIGN PATENT DOCUMENTS, add the following: --

PI 9202817-9A    1/94    Brazil

WO95-16419    6/95

WO96/20666    7/95

WO95/25494    9/95 --.

Column 1, line 41, "at." should read -- al. --.

Column 1, line 50, "fetal" should read -- fecal --.

Column 2, line 3, "fetal" should read -- fecal --.

Column 2, line 24, "previous" should read -- pervious --.

Column 2, line 62, "three" should read -- four --.

Column 3, line 30, "previous" should read -- pervious --.

Column 3, line 56, "from" should read -- front --.

Column 4, line 48, "at." should read -- al. --.

Column 4, line 53, "at." should read -- al. --.

Column 5, line 1, "at." should read -- al. --.

UNITED STATES PATENT AND TRADEMARK OFFICE
CERTIFICATE OF CORRECTION

PATENT NO. : 5,653,703

DATED : August 5, 1997

INVENTOR(S) : DONALD CARROLL ROE ET AL.

It is certified that error appears in the above-identified patent and that said Letters Patent is hereby corrected as shown below:

Column 5, line 5, "at." should read -- al. --.

Column 5, line 21, "bed-sheets" should read -- bedsheets --.

Column 5, line 54, "previous" should read -- pervious --.

Column 7, line 3, delete "to".

Column 7, line 23, "fetal" should read -- fecal --.

Column 7, line 37, "fetal" should read -- fecal --.

Column 7, line 45, "fetal" should read -- fecal --.

Column 8, line 17, "previous" should read -- pervious --.

Column 9, line 23, "from" should read -- front --.

Column 9, line 35, "previous" should read -- pervious --.

Column 10, line 1, "previous" should read -- pervious --.

Signed and Sealed this

Eighteenth Day of August, 1998

Attest:

*Attesting Officer*

BRUCE LEHMAN

*Commissioner of Patents and Trademarks*